(12) United States Patent
Schoebrechts et al.

(10) Patent No.: US 6,399,840 B1
(45) Date of Patent: *Jun. 4, 2002

(54) METHOD FOR THE PREPARATION OF 1,1,1,3,3-PENTACHLOROBUTANE

(75) Inventors: Jean-Paul Schoebrechts, Grez-Doiceau; Véronique Mathieu, Wavre; Francine Janssens, Vilvoopde, all of (BE)

(73) Assignee: Solvay (Societe Anonyme) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/423,258

(22) PCT Filed: Apr. 28, 1998

(86) PCT No.: PCT/EP98/02585

§ 371 (c)(1),
(2), (4) Date: Dec. 30, 1999

(87) PCT Pub. No.: WO98/50329

PCT Pub. Date: Nov. 12, 1998

(30) Foreign Application Priority Data

May 5, 1997 (BE) ............................................. 09700399
Aug. 8, 1997 (BE) ............................................. 09700669

(51) Int. Cl.[7] ......................... C07C 17/266; C07C 17/26
(52) U.S. Cl. ....................................... 570/172; 570/257
(58) Field of Search ................................. 570/172, 257

(56) References Cited

U.S. PATENT DOCUMENTS

| | | | |
|---|---|---|---|
| 3,268,603 A | 8/1966 | Scherling | 570/257 |
| 3,454,657 A | 7/1969 | Decker et al. | 260/651 |
| 3,649,698 A | 3/1972 | Goble et al. | 570/257 |
| 3,651,019 A | 3/1972 | Asscher et al. | |
| 3,862,978 A | 1/1975 | Decker et al. | |
| 5,446,217 A | 8/1995 | Van Der Puy et al. | |
| 5,792,893 A | 8/1998 | Wilson et al. | |
| 5,917,098 A | 6/1999 | Bertocchio et al. | |

FOREIGN PATENT DOCUMENTS

| | | |
|---|---|---|
| EP | 0 729 932 | 4/1996 |
| EP | 0 787 707 | 6/1997 |
| FR | 1288511 | 5/1961 |
| GB | 1146463 | 3/1969 |
| GB | 2 188 929 A | 10/1987 |
| WO | 95/04021 | 2/1995 |
| WO | 95/04022 | 2/1995 |
| WO | 96/01797 | 1/1996 |
| WO | 97/05089 | 2/1997 |
| WO | 97/07083 | 2/1997 |
| WO | 97/15540 | 5/1997 |
| WO | 98/50329 | 11/1998 |
| WO | 98/50330 | 11/1998 |
| WO | 99/07659 | 2/1999 |
| ZA | 98/3775 | 1/2000 |
| ZA | 98/3781 | 1/2000 |

OTHER PUBLICATIONS

Asscher and Vofsi, Chlorine Activation by Redox Transfer, Part II. The addition of Carbon Tetrachloride to Olefins, 1963, p. 1887–1896.

R. Freidlinda et al., "Telomerization of 2–Chloropropene with Carbon Tetrachloride", Bull. Acad. Sci. USSR, 28, pp. 1766–1769 (1979).

Kotora et al., "Selective Additions of Polyhalogenate Compounds to Chloro Substituted Ethenes Catalyzed by a Copper Complex", React. Kinet. Catal. Let. 44, No. 2, pp. 415–419 (1991).

T. Asahara et al., "Telomerization of Binylchloride with Carbon Tetrachloride Initiated by n–butylamine and Metallic Salts", Kogyo Kagaku Zasshi, 72 pp. 1526–1529 (1969).

Belbachir et al., "Reaction avec le tetrachlorure de carbone par catalyse redox", Makromol. Chem 185 pp. 1583–1595 (1984).

Kotora et al., "Addition of Tetrachloromethane to Halogenated Ethenes Catalyzed by Transition Metal Complexes," *Journal of Meolecular Catalysts*, 77:51–60 (1992).

Ullmann's Encyclopedia of Industrial Chemistry, 1992, vol. B4, p. 387–388.

*Primary Examiner*—Sreeni Padmanabhan
*Assistant Examiner*—Sikarl A. Witherspoon
(74) *Attorney, Agent, or Firm*—Connolly Bove Lodge & Hutz LLP

(57) ABSTRACT

1,1,1,3,3-pentachlorobutane is obtained by reacting carbon tetrachloride with 2-chloro-1-propene in the presence of at least one copper (I) or (II) compound as telomerization catalyst. Advantageously, a polar compound can be present in the reaction mixture as solvent, and an amine, an amide or a trialkylphosphine oxide can be present as cocatalyst.

14 Claims, No Drawings

METHOD FOR THE PREPARATION OF 1,1,1,3,3-PENTACHLOROBUTANE

This application is a 371 of PCT/EP98/02585 filed Apr. 28, 1998, now WO98/50329, published Nov. 12, 1998.

The present invention relates to a process for the preparation of 1,1,1,3,3-pentachlorobutane, more particularly by telomerization between carbon tetrachloride and 2-chloro-1-propene. 1,1,1,3,3-pentachlorobutane is of considerable industrial value since it leads, by fluorination, to the corresponding pentafluoro derivative (HFC-365mfc) which can be used in particular as a third generation swelling agent or solvent, which has no harmful effect on the ozone layer and does not contribute to the global warming of the planet by the greenhouse effect.

R. Freidlina et al. (Bull. Acad. Sci. USSR, 28, 1766–69, 1979) obtained 1,1,1,3,3-pentachlorobutane in low yield by reaction between carbon tetrachloride and 2-chloro-1-propene in the presence of iron pentacarbonyl as catalyst, in ethanol or isopropanol. The low yield, on the one hand, and the high toxicity of the catalyst, on the other hand, are such that this synthetic method will be difficult to use industrially.

Another route of access to 1,1,1,3,3-pentachlorobutane, described recently by Kotora and coworkers (React. Kinet. Catal, Lett. 44(2), 415–9, 1991), consists in reacting 1,1,1-trichloroethane with 1,1-dichloroethane in the presence of cuprous chloride and amine. The yield obtained is low (8%) and this synthetic method would thus also be difficult to exploit industrially.

The invention is thus directed towards providing a process which makes it possible to gain access, in a single step and with the use of readily available reagents, to 1,1,1,3,3-pentachlorobutane in excellent yield.

The invention thus relates to a process for the manufacture of 1,1,1,3,3-pentachlorobutane by reaction between carbon tetrachloride and 2-chloro-1-propene in the presence of a catalyst comprising at least one copper (I) compound or a copper (II) compound. In general, copper (II) compounds are preferred.

The copper (I) or (II) compound is preferably chosen from copper halides, copper carboxylates, mixed copper salts and complexes formed with neutral ligands.

The fluorides, chlorides, bromides or iodides are found in particular among the copper (I) or (II) halides the chlorides and iodides are preferred. Copper (II) chloride is particularly preferred.

The hydroxyhalides are found in particular among the mixed copper (I) or (II) salts.

Salts formed from carboxylic acids such as acetic acid, propionic acid, butyric acid, cyclohexanebutyric acid-or benzoic acid are found in particular among the copper (I) or (II) carboxylates. Copper (I) or (II) acetates, i.e. the salts formed using acetic acid, are preferred. Copper (II) cyclohexanebutyrate is most particularly preferred.

Complexes formed with neutral ligands such as phosphines, for instance triphenylphosphine or acetylacetone, are found in particular among the complexes formed with copper (I) or (II) compounds. Copper (II) acetylacetonate is preferred.

Advantageously, the catalyst is chosen from copper (I) or (II) acetate, copper (II) cyclohexanebutyrate, the complex formed between cuprous chloride and triphenylphosphine, copper (II) acetylacetonate, copper (II) hydroxychloride, copper (I) chloride, copper (I) iodide and copper (II) chloride. Among these catalysts, copper (II) chloride, copper (II) acetate, copper (II) hydroxychloride, copper (II) cyclohexanebutyrate and copper (II) acetylacetonate are preferred.

In a batchwise process, the molar ratio between the copper compound used and the 2-chloro-1-propene is generally greater than or equal to 0.001. Advantageously, it is greater than or equal to 0.002. Preferably, it is greater than or equal to 0.005. The molar ratio between the copper compound used and the 2-chloro-1-propene is usually less than or equal to 5. Advantageously, it is less than or equal to 1. Preferably, it is less than or equal to 0.5. In a particularly preferred manner, this ratio is greater than or equal to 0.01 and less than or equal to 0.1.

In a continuous process, the molar ratio between the catalyst used and the 2-chloro-1-propene ranges approximately between the same limits as in a batchwise process,. although it can, however, reach a value of 50.

It is understood that the amount of catalyst used is expressed, in a batchwise process, relative to the initial amount of 2-chloro-1-propene used and, in a continuous process, relative to the stationary amount of 2-chloro-1-propene present in the reactor.

The molar ratio between the carbon tetrachloride and the 2-chloro-1-propene used can vary within a wide range. This ratio is generally greater than or equal to 0.1. Advantageously, this ratio is greater than or equal to 0.5. Preferably, it is greater than or equal to 1. Generally, this ratio is, however, less than or equal to 20. Advantageously, this ratio is less than or equal to 10. Preferably, this ratio is less than or equal to 8.

The reaction conventionally takes place at a temperature greater than or equal to room temperature. Preferably, the temperature is greater than or equal to 40° C. Advantageously, it is greater than or equal to 80° C. In general, the reaction temperature does not exceed 2000° C. Advantageously, in particular with copper (II) hydroxychloride as catalyst, the reaction temperature is greater than or equal to 90° C. and is preferably greater than or equal to 100° C. It is usually less than or equal to 150° C., more precisely less than or equal to 140° C. With copper (II) hydroxychloride, it is most particularly advantageous to carry out the reaction at a temperature close to 130° C.

The reaction time in a batchwise process, or the residence time in a continuous process, depend on various parameters such as the reaction temperature, the concentration of reagents and of catalyst in the reaction mixture and their molar ratios. In general, as a function of these parameters, the residence time or the reaction time can range from 5 seconds to 20 hours.

The pressure is usually greater than or equal to atmospheric pressure and less than or equal to 15 bar. It is advantageously less than or equal to 10 bar. Since the telomerization reaction is generally carried out in liquid phase, the pressure is advantageously chosen, as a function of the temperature of the reaction medium, so as to keep the reaction medium essentially in condensed phase.

In a first embodiment of the process according to the invention, the reaction is carried out in the presence of a solvent. Any solvent in which the reagents form the desired product in satisfactory yield can be used. Advantageously, the reaction solvent is an alcohol, a nitrile, an amide, a lactone, a trialkylphosphine oxide, a trialkyl phosphate or another polar solvent.

Among the alcohols which can be used as reaction solvent are, in particular, methanol, ethanol, isopropanol and tert-butanol. Among the nitrites which can be used as reaction solvent are, in particular, aliphatic nitriles, in particular acetonitrile, propionitrile or adiponitrile, and aromatic nitrites, in particular benzonitrile or tolunitrile. Among the nitrites, propionitrile and adiponitrile are preferred.

Among the amides which can be used as reaction solvent are linear amides such as N,N-dimethylacetamide and N,N-dimethylformamide, and cyclic amides such as N-methylpyrrolidone. Mention may also be made of hexamethylphosphoramide. Among the lactones which can be used as reaction solvent, mention may be made in particular of γ-butyrolactone. Among the trialkylphosphine oxides which can be used as reaction solvent, mention may be made in particular of the compounds of formula (R1R2R3)PO, in which R1, R2 and R3 represent identical or different, preferably linear C3–C10 alkyl groups. Tri(n-butyl)phosphine oxide, tri(n-hexyl)phosphine oxide, tri(n-octyl)phosphine oxide, n-octyldi(n-hexyl)phosphine oxide and n-hexyldi(n-octyl)phosphine oxide and mixtures thereof are selected in particular. Among the trialkyl phosphates which can be used as reaction solvent, mention may be made in particular of the compounds of formula $(RO)_3PO$, in which R represents a preferably linear C3–C10 alkyl group. Tributyl phosphate is selected in particular. As other polar solvents, mention may also be made of 1,3-dimethyl-2-imidazolidinone, dimethyl sulphoxide and tetrahydrofuran. Preferably, the solvent is an amide or a trialkylphosphine oxide. Good results have been obtained in particular with N-methylpyrrolidone, with N,N-dimethylacetamide and with a mixture of tri (n-hexyl) phosphine oxide, tri (n-octyl)phosphine oxide, n-octyldi (n-hexyl)phosphine oxide and n-hexyldi (n-octyl)-phosphine oxide.

The amount of solvent used in the first embodiment of the process according to the invention is not critical. However, too dilute a solution does not favour a high yield or a high degree of conversion. Preferably, the molar ratio of the solvent to the 2-chloro-1-propene is greater than or equal to 0.05. Advantageously, this ratio is greater than or equal to 0.1. The molar ratio of the solvent to the 2-chloro-1-propene is generally less than or equal to 20. Advantageously, it is less than or equal to 15. Preferably, this ratio is greater than or equal to 0.2 and less than or equal to 10. In the reaction medium, the amount of solvent can vary, on a molar basis, from about 5 to about 500 times the amount of catalyst, preferably from about 10 to about 200 times.

In a second, preferred embodiment of the process according to the invention, the reaction is carried out in the presence of a cocatalyst. The cocatalyst can be chosen in particular from amines, amides and trialkylphosphine oxides. As amines which can be used as cocatalyst, mention may be made of aliphatic amines or aromatic amines. Among the aliphatic amines are primary amines, secondary amines and tertiary amines. In general, alkanolamines, alkylamines such as, for example, ethanolamine, n-butylamine, tert-butylamine, n-propylamine, isopropylamine, benzylamine, hexamethylenediamine, diethylamine or triethylamine, or aromatic amines such as pyridine or aniline are used as amine. As amides which can be used as cocatalyst, mention may be made of N-methylpyrrolidone and N,N-dimethylformamide. As trialkylphosphine oxides which can be used as cocatalyst, mention may be made of the same compounds as those which can be used as solvent in the first embodiment of the invention. Aliphatic alkylamines such as n-butylamine, tert-butylamine, n-propylamine and isopropylamine are preferred cocatalysts. Isopropylamine and tert-butylamine are most particularly preferred. The trialkylphosphine oxides are other preferred cocatalysts.

Copper (II) compounds are particularly preferred when the reaction is carried out in the presence of a cocatalyst. Very good results have been obtained with copper (II) acetate as catalyst and tert-butylamine as cocatalyst.

In this second preferred embodiment of the process according to the invention, the reaction temperature can be less than or equal to 120° C. In particular, the presence of the cocatalyst allows the reaction to be carried out at a temperature less than or equal to 100° C. while at the same time retaining a high degree of conversion and excellent selectivity. A temperature close to 90° C. is most particularly recommended.

The molar ratio between the cocatalyst and the 2-chloro-1-propene used is generally greater than or equal to 0.001. Advantageously, this ratio is greater than or equal to 0.005. This ratio is usually less than or equal to 1. Advantageously, this ratio is less than or equal to 0.5. Preferably, this ratio is greater than or equal to 0.01 and less than or equal to 0.25. In a particularly preferred manner, this ratio is greater than or equal to 0.1 and less than or equal to 0.2. The amount of cocatalyst used can vary, on a molar basis, from about 0.1 to about 25 times the amount of catalyst, preferably from about 0.5 to about 20 times.

The presence of a cocatalyst in the reaction mixture does not exclude the use of a nitrile or another compound as solvent.

In this second embodiment of the process according to the invention, carbon tetrachloride can be used both as reagent and solvent. The molar ratio between the carbon tetrachloride and the 2-chloro-1-propene is then greater than or equal to 2. Advantageously, this ratio is greater than or equal to 4. Preferably, this ratio is greater than or equal to 4.5. However, in order to avoid too large a dilution of the reagents, this ratio is generally less than or equal to 10 and is preferably less than or equal to 8. Preferably, this ratio is less than or equal to 6.

The process of the invention thus makes it possible to synthesize 1,1,1,3,3-pentachlorobutane in a single step, starting with readily accessible reagents, with a typical selectivity of greater than 90%.

The 1,1,1,3,3-pentachlorobutane obtained according to the process of the invention is a precursor of the analogous corresponding 1,1,1,3,3-pentafluorobutane (HFC-365mfc), which can readily be obtained by treatment with hydrogen fluoride in the presence of a catalyst such as an antimony salt, a titanium salt, a tantalum salt or a tin salt.

The examples below illustrate the invention in a non-limiting manner. In these examples, the reagents, the solvent and the catalyst were introduced into a 300 ml autoclave whose inner walls are lined with Teflon®. Next, the apparatus was closed hermetically, placed in a vertical oven and the temperature was increased gradually and maintained at the desired value for several hours. Stirring was ensured by a magnetic bar placed in the bottom of the autoclave. At the end of the reaction, the autoclave was allowed to cool and a sample of liquid was withdrawn by syringe and assayed by a chromatographic method in order to determine the degree of conversion of the 2,chloro-1-propene and the selectivity towards 1,1,1,3,3-pentachlorobutane.

In the tables below, the degree of conversion is the ratio, expressed as a percent, between the amount of 2-chloro-1-propene used minus the amount unconverted at the end of the reaction and the amount used; the selectivity towards 1,1,1,3,3-pentachlorobutane is the ratio, expressed as a percent, between the amount of 1,1,1,3,3-pentachlorobutane formed and the amount of 1,1,1,3,3-pentachlorobutane which would have been formed if all of the 2-chloro-1-propene converted had generated 1,1,1,3,3-pentachlorobutane.

EXAMPLES 1 to 4

In these examples, 1,1,1,3,3-pentachlorobutane was prepared in the presence of various nitrites and in the presence of a mixture containing 20% CuCl and 80% CuClOH (symbolized as CuCl—CuClOH hereinbelow) as copper compound. The 2-chloro-1-propene/$CCl_4$/CuCl—CuClOH/ nitrile molar ratio was 1/2/0.01/1. The reaction took place at 130° C. for 13 hours. The results obtained are collated in Table I.

TABLE I

| Example | Nitrile | Conversion | Selectivity |
|---|---|---|---|
| 1 | Propionitrile | 94 | 100 |
| 2 | Benzonitrile | 92 | 92 |
| 3 | Tolunitrile | 94 | 91 |
| 4 | Adiponitrile | 97 | 96 |

EXAMPLE 5

Example 1 was repeated with a 2-chloro-1-propene/nitrile molar ratio of 1/0.5. A degree of conversion of 85% and a selectivity of 85% were obtained.

EXAMPLE 6

Example 1 was repeated with a 2-chloro-1-propene/nitrile molar ratio of 1/4. A degree of conversion of 90% and a selectivity of 89% were obtained.

EXAMPLE 7

Example 6 was repeated using anhydrous copper (II) chloride as catalyst. A degree of conversion of 92% and a selectivity of 98% were obtained.

EXAMPLES 8 and 9

In these examples, Example 6 was repeated at various molar ratios between the 2-chloro-1-propene and the CuCl—CuClOH. The 2-chloro-1-propene/$CCl_4$/ propionitrile molar ratio was 1/2/4. The results obtained are collated in Table II.

TABLE II

| Example | CuCl—CuClOH/ 2-chloro-1-propene molar ratio | Conversion | Selectivity |
|---|---|---|---|
| 8 | 0.10 | 96 | 99 |
| 9 | 0.06 | 98 | 92 |

EXAMPLE 10

In this example, Example 6 was repeated at a temperature of 150° C. A degree of conversion of 99% and a selectivity of 91% were obtained.

EXAMPLES 11 and 12

In these examples, 1,1,1,3,3-pentachlorobutane was prepared in the presence of various amines and in the presence of CuCl—CuClOH. The 2-chloro-1-propene/$CCl_4$/CuCl—CuClOH/amine molar ratio was 1/5/0.05/0.1. The reaction took place at 90° C. for 2 hours. The results obtained are collated in Table III.

TABLE III

| Example | Amine | Conversion | Selectivity |
|---|---|---|---|
| 11 | Isopropylamine | 95 | 96 |
| 12 | tert-Butylamine | 79 | 95 |

EXAMPLE 13

Example 12 was repeated with copper (II) acetate as catalyst and a reaction time of 1 hour at 90° C. The 2-chloro-1-propene/$CCl_4$/$Cu(COOCH_3)_2$/amine molar ratio was 1/5/0.05/0.15. A degree of conversion of 96% and selectivity of 97% were obtained.

EXAMPLES 14 to 20

Example 11 was repeated with various copper compounds. The results are collated in Table IV.

TABLE IV

| Example | Copper compound | Conversion | Selectivity |
|---|---|---|---|
| 14 | $(CH_3COO)_2Cu$ | 88 | 98 |
| 15 | CuI | 89 | 98 |
| 16 | $Cu(PPh_3)_3Cl$ | 66 | 99 |
| 17 | CuBr | 68 | 98 |
| 18 | $(C_{10}H_{17}O_2)_2Cu$* | 92 | 98 |
| 19 | $(C_5H_7O_2)_2Cu$** | 82 | 93 |
| 20 | CuClOH | 87 | 96 |

*copper (II) cyclohexanebutyrate
**copper (II) acetylacetonate

EXAMPLE 21 (not in accordance with the invention)

Example 6 was repeated, but in the absence of copper compound. No formation of 1,1,1,3,3-pentachlorobutane is observed.

EXAMPLES 22 to 25

1,1,1,3,3-Pentachlorobutane was prepared in the presence of various solvents and copper (II) acetylacetonate as catalyst. The reaction time was 2 hours. The molar ratio of the reagents, the reaction temperatures and the results obtained are collated in Table V.

EXAMPLES 26–27

1,1,1,3,3-Pentachlorobutane was prepared starting with 2-chloro-1-propene and carbon tetrachloride in the presence of copper (II) acetylacetonate as catalyst and a mixture of 4 trialkylphosphine oxides (tri(n-hexyl)phosphine oxide, tri(n-octyl)phosphine oxide, n-octyldi(n-hexyl)phosphine oxide and n-hexyldi(n-octyl)phosphine oxide), sold by Cytec under the name Cyanex® 923. The reaction time was 2 hours. The molar ratios of the reagents, the reaction temperatures and the results obtained are also presented in Table V.

TABLE V

| Ex. | Solvent | 2-CPe/CCl$_4$/ Cu(acac)$_2$/ solvent molar ratio | Temperature | Conversion | Selectivity |
|---|---|---|---|---|---|
| 22 | N-methylpyrrolidone | 1/2/0.06/3.8 | 100° C. | 96 | 97 |
| 23 | N,N-dimethylacetamide | 1/3.5/0.06/4.1 | 90° C. | 67 | 99 |
| 24 | 1,3-dimethyl-2-imidazolidinone | 1/2.2/0.05/3.2 | 90° C. | 46 | 97 |
| 25 | N,N-dimethylformamide | 1/1.9/0.06/5.7 | 100° C. | 72 | 96 |
| 26 | Cyanex ® 923 | 1/1.8/0.047/0.99 | 90° C. | 86 | 95 |
| 27 | Cyanex ® 923 | 1/5/0.05/0.24 | 90° C. | 88 | 95 |

EXAMPLE 28

Example 24 was repeated with copper (II) acetate as catalyst. A degree of conversion of 55% and a selectivity towards 1,1,1,3,3-pentachlorobutane of 94% were obtained.

EXAMPLE 29

1,1,1,3,3-Pentachlorobutane was prepared in the presence of CuCl$_2$ as catalyst and N-methylpyrrolidone as solvent. The 2-chloro-1-propene/CCl$_4$/CuCl$_2$/N-methylpyrrolidone molar ratio was 1/2.2/0.05/3.3. After reaction for 5 hours at 115° C., the degree of conversion was 100% and the selectivity towards 1,1,1,3,3-pentachlorobutane was 94%.

What is claimed is:

1. Process for the preparation of 1,1,1,3,3-pentachlorobutane by reacting carbon tetrachloride with 2-chloro-1-propene in the presence of a telomerization catalyst, wherein the catalyst comprises at least one copper (II) compound.

2. Process according to claim 1, wherein the copper compound is copper halides, mixed copper salts, copper carboxylates and complexes with a phosphine or acetylacetone, or mixtures thereof.

3. Process according to claim 2, wherein the catalyst is chosen from copper (II) acetate, copper (II) hydroxychloride, copper (II) cyclohexane-butyrate, copper (II) acetylacetonate and copper (II) chloride.

4. Process according to claim 1, wherein the reaction takes place in the presence of a solvent.

5. Process according to claim 4, wherein the solvent is a nitrile, an amide or a trialkylphosphine oxide.

6. Process according to claim 5, wherein the solvent is N-methylpyrrolidone, N, N-dimethylacetamide, tri(n-hexyl) phosphine oxide, tri(n-octyl) phosphine oxide, n-octyldi (n-hexyl)phosphine oxide or n-hexyldi (n-octyl) phosphine oxide, or mixtures thereof.

7. Process according to claim 1, wherein the reaction takes place in the presence of a cocatalyst.

8. Process according to claim 7, wherein the cocatalyst is an amine.

9. Process according to claim 8, wherein the amine is isopropylamine or tert-butylamine.

10. Process according to claim 1, wherein the reaction takes place at a temperature greater than or equal to 40° C. and less than or equal to 200° C.

11. A process for the synthesis of 1,1,1,3,3-pentafluorobutane (HFC-365mfc) comprising fluorinating 1,1,1,3,3-pentachlorobutane obtained by the process as claimed in claim 1.

12. The process as claimed in claim 11, wherein 1,1,1,3,3-pentachlorobutane is fluorinated by the treatment with hydrogen fluoride.

13. The process as claimed in claim 12, wherein the treatment with hydrogen fluoride is carried out in the presence of the catalyst.

14. The process as claimed in claim 13, wherein the catalyst is antimony salt, titanium salt, tantalum salt or tin salt.

* * * * *

UNITED STATES PATENT AND TRADEMARK OFFICE
CERTIFICATE OF CORRECTION

PATENT NO. : 6,399,840 B1 Page 1 of 1
DATED : June 4, 2002
INVENTOR(S) : Schoebrechts et al.

It is certified that error appears in the above-identified patent and that said Letters Patent is hereby corrected as shown below:

Column 8,
Line 13, delete "n-octyidi" and insert -- n-octyldi --.

Signed and Sealed this

Twenty-ninth Day of October, 2002

Attest:

JAMES E. ROGAN
Attesting Officer    Director of the United States Patent and Trademark Office